United States Patent
Artmeier

(10) Patent No.: US 7,063,460 B2
(45) Date of Patent: Jun. 20, 2006

(54) UROLOGICAL WORKING PLACE

(75) Inventor: Theo Artmeier, Groebenzell (DE)

(73) Assignee: Dornier MedTech Systems GmbH, Wessling (DE)

( * ) Notice: Subject to any disclaimer, the term of this patent is extended or adjusted under 35 U.S.C. 154(b) by 0 days.

(21) Appl. No.: 10/764,346

(22) Filed: Jan. 23, 2004

(65) Prior Publication Data

(30) Foreign Application Priority Data

Jan. 23, 2003 (DE) .............................. 103 02 612

(51) Int. Cl.
*H05G 1/02* (2006.01)

(52) U.S. Cl. ...................................... 378/196; 378/197

(58) Field of Classification Search ................ 378/195, 378/209, 205, 196, 198, 197, 206, 64, 65; 601/4; 606/128
See application file for complete search history.

(56) References Cited

U.S. PATENT DOCUMENTS

| | | | |
|---|---|---|---|
| 48,847 A | 7/1865 | Smith | |
| 1,750,129 A | 3/1930 | Romine | |
| 4,336,858 A | 6/1982 | Loyzim | |
| 4,494,622 A | 1/1985 | Thompson | |
| 4,756,016 A * | 7/1988 | Grady et al. ................ | 378/197 |
| 4,829,986 A | 5/1989 | Eichler et al. | |
| 5,072,722 A | 12/1991 | Granz | |
| 5,072,960 A | 12/1991 | Sperko | |
| 5,090,401 A | 2/1992 | Schwieker | |
| 5,149,030 A | 9/1992 | Cockrill | |
| 5,285,772 A * | 2/1994 | Rattner .......................... | 601/4 |
| 5,301,659 A | 4/1994 | Brisson et al. | |
| 5,409,002 A * | 4/1995 | Pell ............................... | 601/4 |
| 5,572,569 A | 11/1996 | Benoit et al. | |
| 5,642,898 A | 7/1997 | Wise | |
| 5,836,898 A * | 11/1998 | Schwieker ..................... | 601/4 |
| 6,036,661 A | 3/2000 | Schwarze et al. | |
| 6,119,034 A | 9/2000 | Herrmann et al. | |
| 6,276,471 B1 | 8/2001 | Kratzenberg et al. | |
| 6,386,560 B1 | 5/2002 | Calender | |
| 2001/0048732 A1 * | 12/2001 | Wilson et al. ................ | 378/21 |
| 2002/0125664 A1 | 9/2002 | Eriksson et al. | |
| 2003/0078523 A1 * | 4/2003 | Burkhardt et al. ............. | 601/2 |

FOREIGN PATENT DOCUMENTS

| | | |
|---|---|---|
| DE | 17 69 521 U | 10/1957 |
| DE | GM 75 32 292 | 3/1977 |
| DE | GM 94 14 692 U1 | 12/1994 |
| DE | 44 43 495 | 6/1996 |
| DE | 196 31 246 A1 | 2/1998 |
| DE | 197 02 829 A1 | 7/1998 |

(Continued)

*Primary Examiner*—Edward J. Glick
*Assistant Examiner*—Irakli Kiknadze
(74) *Attorney, Agent, or Firm*—King & Spalding LLP

(57) ABSTRACT

A urological working place is provided that can include a U-bow with an x-ray source arranged at one end and an image processing device arranged at the other end, wherein the image processing device cooperates with the x-ray source. An examination table is releasably secured to the U-bow and replaceable by an alternate examination table that is independent of the movements of the U-bow. The x-ray source and the image processing device are displaceable relative to the U-bow individually and synchronously in a transverse direction, and the U-bow is supported in a lower area thereof so that it is tiltable in the longitudinal direction of the examination table.

32 Claims, 2 Drawing Sheets

FOREIGN PATENT DOCUMENTS

| | | |
|---|---|---|
| DE | 197 18 511 C2 | 11/1998 |
| DE | 198 43 680 | 2/2000 |
| DE | 101 11 800 A1 | 10/2002 |
| DE | 102 06 193 | 7/2003 |

* cited by examiner

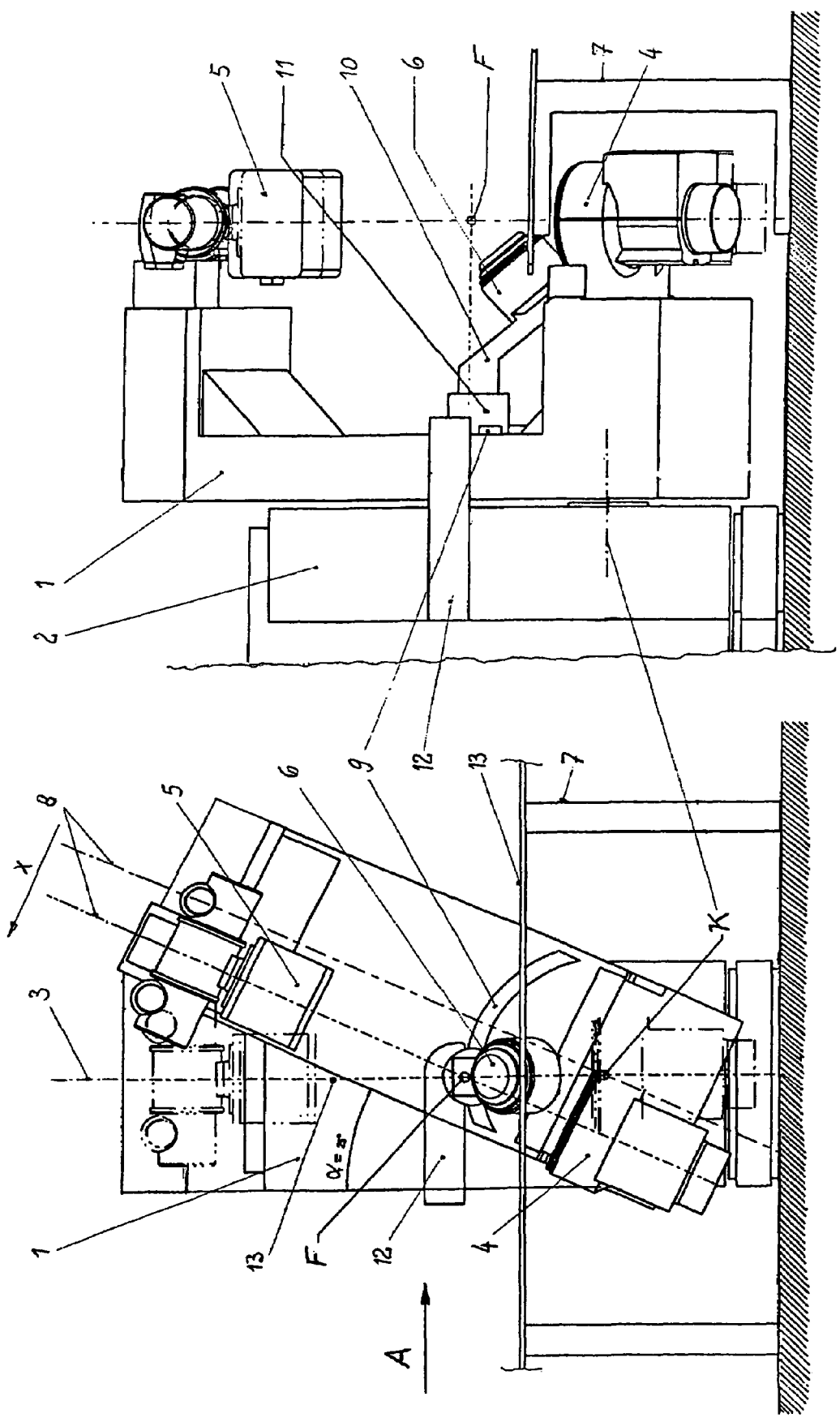

UROLOGICAL WORKING PLACE

CROSS REFERENCE TO RELATED APPLICATION

This application claims priority to co-pending German Patent Application No. 103 02 612.6, which was filed on Jan. 23, 2003 and is incorporated herein by reference.

FIELD OF THE INVENTION

The present invention generally relates to a urological working place, and more particularly, to a urological working place that can be used for lithotripsy treatment.

BACKGROUND OF THE INVENTION

A urological working place comprising an x-ray source at the upper end of a so-called U-bow and a radiation reception array at the lower end of the U-bow is known, for example, from German Patent No. DE 198 43 680, which is incorporated herein by reference. In that example, the examination table for the patient is fixedly attached to a U-bow. The examination table is located between an x-ray examination unit comprising an x-ray source and a radiation reception means. The x-ray examination unit is displaceable relative to the examination table in the x-direction and in the y-direction. The individual components of the x-ray examination unit are adapted to be moved individually, preferably, however, in synchronism with one another. In the case of a vertical adjustment of the U-bow, the examination table is vertically moved as well. When the U-bow is tilted, the examination table is tilted as well, without any change in the relation between the examination table and the x-ray examination unit. The tilting axis extends approximately through the examination table.

The above described features are clearly advantageous for examinations in which the gravity-dependent flow behavior of contrast media in a patient's uro-tract is to be diagnosed, but may be less advantageous when such a urological working place is to be used for carrying out a treatment by lithotripsy. For example, when a lithotripsy is being executed, the location of the concrement to be destroyed needs to be located within the patient's body. To carry out this locating step, the U-bow needs to be tiltable independently of the examination table, and the tilting axis of the U-bow needs to extend through the patient's body.

Therefore, there is a need in the art to provide a urological working place that can be used for treatment by lithotripsy, in addition to its use for diagnostic and indicatory functions.

SUMMARY OF THE INVENTION

The present invention, according to exemplary embodiments described below, provides a urological working place that can be used for treatment by lithotripsy, in addition to use for diagnostic and indicatory functions. In accordance with exemplary embodiments of the present invention, when an attending physician executes locating steps, features of the present invention permit a displacement of the x-ray beam by displacing the respective radiation source on a tilted U-bow in the x-direction into the focus of a therapy head of an adjacent lithotripter so as to re-establish the iso-center of the therapeutic beam of the lithotripter and of the x-rays in the tilted condition of the U-bow.

One special advantage of the present invention, in accordance with the following exemplary embodiments, is that it also provides for an existing urological working place to be converted into a lithotripter working place quickly and with little technical and economic expenditure. Thus, in many cases, the acquisition of an expensive, independent lithotripter working place can be avoided as a result of the present invention. Additionally, an examination table used in the urological working place, according to exemplary embodiments of the present invention, does not need to be vertically adjustable and may include a lateral recess for unhindered use of a lithotripter device.

These and other aspects of the invention will be described further in the detailed description of exemplary embodiments below in connection with the drawings and the claims.

BRIEF DESCRIPTION OF THE DRAWINGS

The accompanying drawings are incorporated into and form a part of the specification for the purpose of explaining the principles of the invention. The drawings are not to be construed as limiting the invention to only the illustrated and described examples of how the invention can be made and used. Further features and advantages will become apparent from the following detailed description of exemplary embodiments of the invention as illustrated in the accompanying drawings, wherein:

FIG. 1 shows an exemplary frontal view of a urological working place that can be used for lithotripsy treatment in accordance with exemplary embodiments of the present invention.

FIG. 2 shows an exemplary side view of the urological working place viewed from the direction of sight "A" according to FIG. 1.

DETAILED DESCRIPTION OF THE EXEMPLARY EMBODIMENTS

Figure 3:
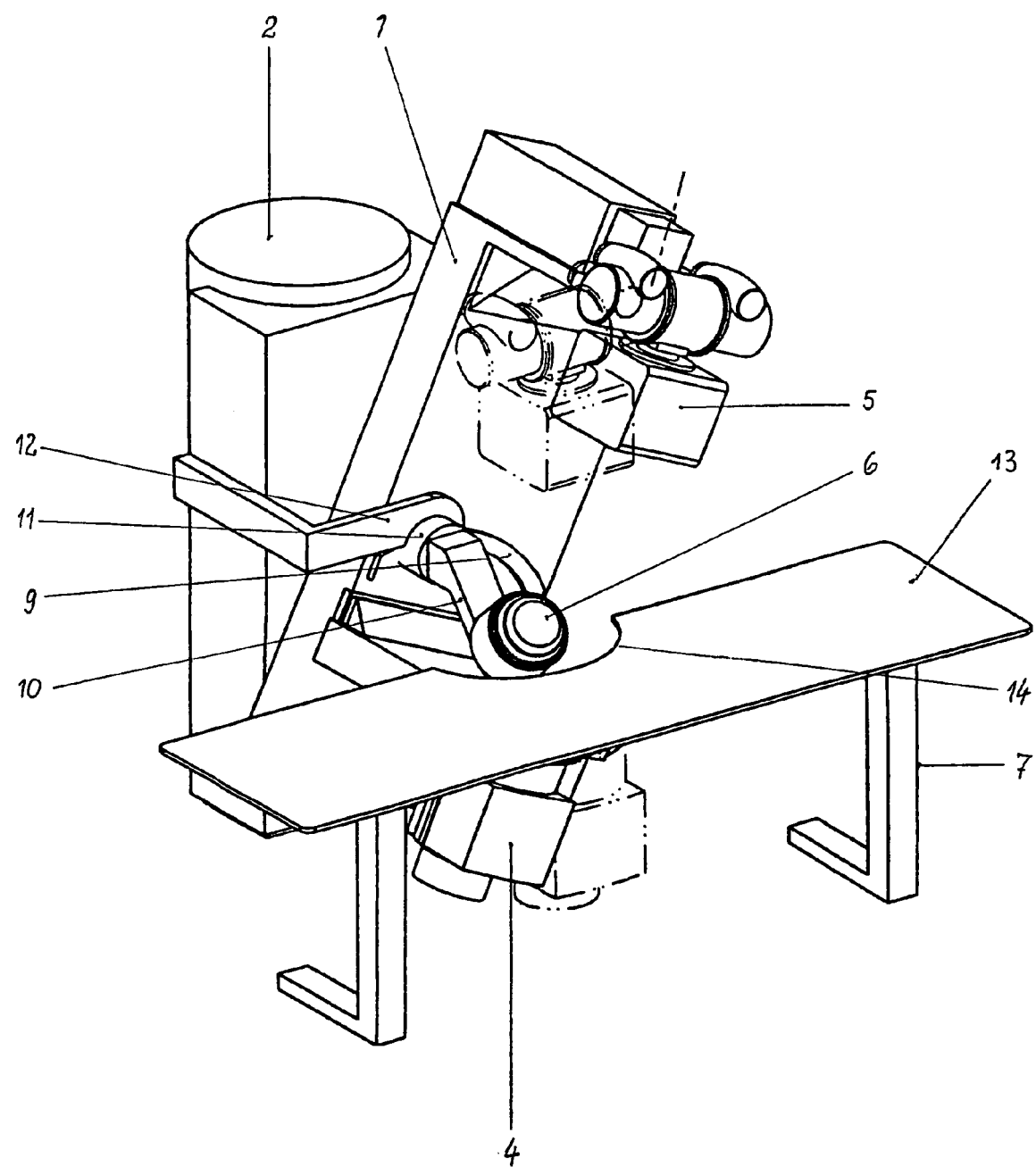
FIG. 3 shows an exemplary perspective view of the urological working place in accordance with FIGS. 1 and 2.

Proceeding from a urological working place, the medical apparatus according to FIGS. 1–3 comprises a so-called U-bow 1. The U-bow 1 typically comprises a U-shaped carrier which is tiltably mounted on a base frame 2 in a support with an axis K. The axis K extends horizontally in the vertical center plane 3 of the U-bow 1 and below the support plate 13 of an examination table 7, when viewed in the vertical direction. An examination table 17 is releasably secured to the U-bow 1 and replaceable by the alternate examination table 7 that is independent of the movements of the U-bow 1. The upper end of the U-bow 1 has arranged thereon, in a manner which may be known in the art, an x-ray source 5 which cooperates with an image processing device (or means) 4 at the other end of the U-bow 1. The x-ray source 5 and the image processing device 4 define together an x-ray unit.

According to exemplary embodiments of the present invention, the urological working place can have associated therewith (and/or further comprise) a therapy head 6 of a lithotripter, whose focus F is positioned above the examination table 7 in the center plane 3. At the vertical position of the U-bow 1, the focus F also intersects a central line 8 of the x-rays. When the U-bow 1 is titled about the axis K, the central line 8 of the x-rays is pivoted away from the focus F. For executing the second locating step on a patient, the x-ray source 5 and the image processing device 4, in synchronism therewith, can be displaced on the U-bow 1 in the x-direction (i.e., parallel to the support surface of the x-ray source 5 and the support surface of the image processing device 4 on the U-bow 1) until the central line 8, which represents the central ray of the x-ray unit, intersects the focus F again. The x-ray source 5 and the image processing device 4 are typically adapted to be displaced relative to the U-bow 1 individually and also synchronously in the transverse direction.

In accordance with exemplary embodiments of the present invention, as illustrated in FIGS. 1–3, the U-bow 1 can be tilted about the axis K through an angle of substantially 25° in the course of the locating process, whereupon the units 4 and 5 are displaced on the U-bow 1 by approximately 140 mm in the x-direction. For fixedly positioning the therapy head 6 within the working place, the U-bow 1 has provided thereon a preferably circularly bent guide segment 9 whose center is positioned on the tilting axis K as well. Making use of an arm 10 and a slide (or slide mechanism) 11, the therapy head 6 can in this way be guided on the guide segment 9 (which is secured in position on the U-bow 1) in a frictional and/or positive engagement therewith and can be retained at its original position by a holder 12 secured to the base frame 2, when the U-bow 1 is tilted about the axis K.

As additionally illustrated in FIGS. 1–3, the support plate 13 of an examination table 7 can be located between the focus F of the therapy head 6 and the axis K. A simple relax bed can be used for this purpose in accordance with exemplary embodiments of the present invention. For executing locating steps on the patient, it may be advantageous to implement the support plate 13 such that it is vertically adjustable. This type of adjustability can be realized, for example, by the legs of the examination table 7 in manners known in the art.

Since the U-bow 1 is vertically adjustable, it is also possible to use an alternate examination table, such as a bed, that is not vertically adjustable and/or is independent of the movements of the U-bow 1. For example, the examination table 17 can be replaced with an alternate examination table 7 that is not vertically adjustable and is not secured to the U-bow 1. The examination table 17 can be releasably secured to the U-bow 1 and replaceably by the alternate examination table 7 that is independent of the U-bow 1. This alternate examination table 7 is preferably adjustable in the x-y direction. Additionally, as illustrated in FIG. 3, a semicircular recess 14 on the support plate 13 in the area of use of the therapy head 6 may be provided (e.g., for structural reasons) to ensure an unhindered use of a lithotripter.

While the invention has been described above with respect to exemplary embodiments, it will be apparent to those skilled in the art that various modifications, variations and improvements of the invention may be made in light of the above description and within the purview of the appended claims without departing from the spirit and intended scope of the invention. In regard to the foregoing description of exemplary embodiments of the invention, areas which are known to those of ordinary skill in the art may not have been described in detail, in order to facilitate a clear and concise description of the invention. Accordingly, it should be understood that the invention is not to be limited by the specific exemplary embodiments, but only by the scope of the appended claims.

What is claimed is:

1. A urological working place, comprising:
a U-bow, having arranged thereon an x-ray source at one end thereof and an image processing device at the other end thereof, the image processing device cooperating with the x-ray source to define an x-ray unit; and
an examination table releasably secured to the U-bow and replaceable by an alternate examination table that is independent of the movements of the U-bow,
wherein the x-ray source and the image processing device are displaceable relative to the U-bow individually and synchronously in a transverse direction, and the U-bow is supported in a lower area thereof so that it is tiltable in the longitudinal direction of the examination table.

2. The urological working place of claim 1, wherein the U-bow is structured to have associated therewith a lithotripter having a focus located above a support plate of the alternate examination table, wherein a central beam of the x-ray unit intersects the focus at a vertical starting position of the U-bow in a laterally non-displaced condition of the x-ray unit, and wherein the x-ray unit can be displaced until the central beam intersects the focus when the U-bow is in a tilted condition.

3. The urological working place of claim 2, further comprising a circularly bent guide segment on the U-bow, for reliably positioning a therapy head of the lithotripter, the therapy head having a center located on a tilting axis of the U-bow, wherein when the U-bow is tilted about the tilting axis, the therapy head can be retained at an original position by a support that is independent of the movements of the U-bow.

4. The urological working place of claim 2, wherein the U-bow is tiltable in a defined angle, and wherein the x-ray unit is displaceable on the U-bow by a defined length and in a defined direction.

5. The urological working place of claim 2, wherein a support plate of the alternate examination table comprises a lateral recess to allow unhindered use of a therapy head in conjunction with the U-bow.

6. The urological working place of claim 2, wherein the alternate examination table is vertically adjustable.

7. The urological working place of claim 2, wherein the x-ray source is arranged at an upper end of the U-bow, and wherein the image processing device is arranged at a lower end of the U-bow.

8. The urological working place of claim 1, further comprising a circularly bent guide segment on the U-bow, for reliably positioning a therapy head of a lithotripter, the therapy head having a center located on a tilting axis of the U-bow, wherein when the U-bow is tilted about the tilting axis, the therapy head can be retained at an original position by a support that is independent of the movements of the U-bow.

9. The urological working place of claim 8, wherein the U-bow is tiltable in a defined angle, and wherein the x-ray unit is displaceable on the U-bow by a defined length and in a defined direction.

10. The urological working place of claim 8, wherein a support plate of the alternate examination table comprises a lateral recess to allow unhindered use of a therapy head in conjunction with the U-bow.

11. The urological working place of claim 8, wherein the alternate examination table is vertically adjustable.

12. The urological working place of claim 8, wherein the x-ray source is arranged at an upper end of the U-bow, and wherein the image processing device is arranged at a lower end of the U-bow.

13. The urological working place of claim 1, wherein the U-bow is tiltable in a defined angle, and wherein the x-ray unit is displaceable on the U-bow by a defined length and in a defined direction.

14. The urological working place of claim 13, wherein a support plate of the alternate examination table comprises a lateral recess to allow unhindered use of a therapy head in conjunction with the U-bow.

15. The urological working place of claim 13, wherein the alternate examination table is vertically adjustable.

16. The urological working place of claim 13, wherein the x-ray source is arranged at an upper end of the U-bow, and wherein the image processing device is arranged at a lower end of the U-bow.

17. The urological working place of claim 1, wherein a support plate of the alternate examination table comprises a lateral recess to allow unhindered use of a therapy head in conjunction with the U-bow.

18. The urological working place of claim 17, wherein the alternate examination table is vertically adjustable.

19. The urological working place of claim 17, wherein the x-ray source is arranged at an upper end of the U-bow, and wherein the image processing device is arranged at a lower end of the U-bow.

20. The urological working place of claim 1, wherein the alternate examination table is vertically adjustable.

21. The urological working place of claim 20, wherein the x-ray source is arranged at an upper end of the U-bow, and wherein the image processing device is arranged at a lower end of the U-bow.

22. The urological working place of claim 1, wherein the x-ray source is arranged at an upper end of the U-bow, and wherein the image processing device is arranged at a lower end of the U-bow.

23. A urological working place, comprising:
   an x-ray unit comprising an image processing device cooperating with an x-ray source; and
   a U-bow having arranged thereon the x-ray source at one end thereof and the image processing device at an opposite end thereof,
   wherein the x-ray source and the image processing device are displaceable in a transverse direction relative to the U-bow, and the U-bow is tiltable relative to a vertical axis.

24. The urological working place of claim 23, wherein the x-ray source and the image processing device are displaceable synchronously in a transverse direction relative to the U-bow.

25. The urological working place of claim 23, wherein the x-ray source and the image processing device are displaceable individually in a transverse direction relative to the U-bow.

26. The urological working place of claim 23, wherein the U-bow is supported in a lower area thereof so that it is tiltable relative to the vertical axis.

27. The urological working place of claim 23, wherein the U-bow is structured to have associated therewith a lithotripter having a focus located above a support plate of an examination table, wherein a central beam of the x-ray unit intersects the focus at a vertical starting position of the U-bow in a laterally non-displaced condition of the x-ray unit, and wherein the x-ray unit can be displaced relative to the U-bow until the central beam intersects the focus when the U-bow is in a tilted condition.

28. The urological working place of claim 23, further comprising a circularly bent guide segment on the U-bow, for reliably positioning a therapy head of a lithotripter, the therapy head having a center located on a tilting axis of the U-bow, wherein when the U-bow is tilted about the tilting axis, the therapy head can be retained at an original position by a support that is independent of the movements of the U-bow.

29. The urological working place of claim 23, wherein the U-bow is tiltable in a defined angle, and wherein the x-ray unit is displaceable on the U-bow by a defined length and in a defined direction.

30. The urological working place of claim 23, further comprising an examination table that is independent of the movements of the U-Bow, wherein a support plate of the examination table comprises a lateral recess to allow unhindered use of a lithotripter therapy head in conjunction with the U-bow.

31. The urological working place of claim 30, wherein the examination table is vertically adjustable.

32. The urological working place of claim 23, wherein the x-ray source is arranged at an upper end of the U-bow, and wherein the image processing device is arranged at a lower end of the U-bow.

* * * * *